US00PP09155P

United States Patent [19]

VandenBerg

[11] Patent Number: Plant 9,155

[45] Date of Patent: Jun. 6, 1995

[54] CHRYSANTHEMUM PLANT NAMED 'JASPER'

[75] Inventor: Cornelis P. VandenBerg, Salinas, Calif.

[73] Assignee: Yoder Brothers, Inc., Barberton, Ohio

[21] Appl. No.: 280,524

[22] Filed: Jul. 26, 1994

[51] Int. Cl.[6] ..... A01H 5/00

[52] U.S. Cl. ..... Plt./82.5

[58] Field of Search ..... Plt. 82.5, 82.4, 74.1

*Primary Examiner*—Howard J. Locker

*Attorney, Agent, or Firm*—Foley & Lardner

[57] ABSTRACT

A Chrysanthemum plant named Jasper particularly characterized by its flat capitulum form; anemone capitulum type; red ray floret color with greenish overlaid red cushion; diameter across face of capitulum of 64 to 70 mm when fully opened, when grown as a pinched spray pot mum; photoperiodic flowering response to short days of 53 to 60 days; plant height, with 14 to 17 long days after sticking unrooted cuttings, and with 0 to 2 applications of 2500 ppm B-9 SP, ranges from 23 to 33 cm when grown as a pinched pot mum with four cuttings in a 15 cm pot; branching pattern is spreading and prolific, each plant having 4 to 5 laterals after pinch; and recommended as spray pot mum.

3 Drawing Sheets

The present invention comprises a new and distinct cultivar of Chrysanthemum, botanically known as *Dendranthema grandiflora,* and referred to by the cultivar name Jasper.

Jasper, identified as 4446 (91-389004), was originated from a cross made by Cornelis P. VandenBerg in a controlled breeding program in Salinas, Calif., in 1991.

The female parent of Jasper was an unnamed seedling identified as 4795 (85-914004) and described as a pot spray mum with a flat capitulum form; anemone capitulum type; light pink ray floret color; diameter across face of capitulum of 51 to 54 mm when grown as a spray pot mum; flowering response to short days in Salinas, Calif. of 53 to 60 days; plant height of 23 to 33 cm when grown with 15 to 16 long days after sticking unrooted cuttings prior to start of short days and 0 to 2 applications of 2500 ppm B-9 SP; and a branching pattern of 3 to 4 laterals developing after pinch. The female parent was discarded from all programs on Dec. 20, 1991.

The male parent of Jasper was the cultivar identified as Lucido, disclosed in U.S. Plant Pat. No. 6,586, and described as a pot spray mum with a flat capitulum form; daisy capitulum type; red ray floret color; diameter across face of capitulum of 70 to 83 mm when grown as a spray pot mum; flowering response to short days in Salinas, Calif. of 56 to 60 days; plant height of 23 to 30 cm when grown with 15 to 16 long days after sticking unrooted cuttings prior to start of short days and 1 to 2 applications of 2500 ppm B-9 SP; and a branching pattern of 5 laterals developing after pinch. The ranges of measurements of Lucido are somewhat greater than the measurements disclosed in U.S. Plant Pat. No. 6,586 for Lucido. This is based on continuing flowering trials of Lucido.

Jasper was discovered and selected as one flowering plant within the progeny of the stated cross by Cornelis P. VandenBerg in Jan. 1992, in a controlled environment in Salinas, Calif.

The first act of asexual reproduction of Jasper was accomplished when vegetative cuttings were taken from the initial selection in Mar. 1992 in a controlled environment in Salinas, Calif., by technicians working under supervision of Cornelis, P. VandenBerg.

Horticultural examination of controlled flowerings of successive plantings has shown that the unique combination of characteristics as herein disclosed for Jasper are firmly fixed and are retained through successive generations of asexual reproduction.

Jasper has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Jasper, which, in combination, distinguish this Chrysanthemum as a new and distinct cultivar:

1. Flat capitulum form.
2. Anemone capitulum type.
3. Red ray floret color with greenish overlaid red cushion.
4. Diameter across face of capitulum of 64 to 70 mm when fully opened, when grown as a pinched spray pot mum.
5. Photoperiodic flowering response to short days of 53 to 60 days.
6. Plant height, with 14 to 17 long days after sticking unrooted cuttings, and with 0 to 2 applications of 2500 ppm B-9 SP, ranges from 23 to 33 cm when grown as a pinched pot mum with four cuttings in a 15 cm pot.
7. Branching pattern is spreading and prolific, each plant having 4 to 5 laterals after pinch.
8. Recommended as spray pot mum.

The accompanying photographic drawings show typical inflorescence and leaf characteristics of Jasper, with the colors being as nearly true as possible with illustrations of this type.

Sheet 1 is a color photograph of Jasper grown as a pinched spray pot mum with four cuttings in a 15 cm pot.

Sheet 2 is a black and white photograph of three views of the inflorescence of Jasper.

Sheet 3 is a black and white photograph showing the upper and under sides of the leaves of Jasper at three stages of development (mature, intermediate and immature).

In sheets 2 and 3 a measuring tape in centimeters has been added.

Of the commercial cultivars known to the inventor, the most similar in comparison to Jasper is the male parent Lucido. Reference is made to attached Chart A, which compares certain characteristics of Jasper to the same characteristics of Lucido.

Similar traits are capitulum form, ray floret color, flowering response to short days, branching pattern, and recommended use. The capitulum type of Jasper is described as anemone, while Lucido has a daisy capitulum type. Jasper also has a smaller diameter of capitulum than Lucido, and a taller plant height.

In the following description color references are made to The Royal Horticultural Society Colour Chart. The color values were determined on plant material grown as a pinched spray pot mum in Salinas, Calif. on Apr. 29, 1994.

Classification:

*Botanical.*—*Dendranthema grandiflora* cv Jasper.

*Commercial.*—Anemone spray pot mum.

INFLORESCENCE

A. Capitulum:

*Form.*—Flat.

*Type.*—Anemone.

*Diameter across face.*—64 to 70 mm when fully opened.

B. Corolla of ray florets:

*Color (general tonality from a distance of three meters).*—Red, with greenish overlaid red anemone cushion.

*Color (upper surface).*—Closest to 46A to 46B.

*Color (under surface).*—179A to 179C.

*Shape.*—See photograph.

C. Corolla of disc florets:

*Color (mature).*—46A, slightly overlaid with 162A.

*Color (immature).*—46A, strongly overlaid with 162A.

D. Reproductive organs:

*Androecium.*—Present on disc florets only; no pollen.

*Gynoecium.*—Present on both ray and disc florets.

PLANT

A. General appearance:

*Height.*—23 to 33 cm when grown as a pinched pot mum with four cuttings in a 15 cm pot with 14 to 17 long days after direct sticking unrooted cuttings prior to start of short days, and with 0 to 2 applications of 2500 ppm B-9 SP.

*Branching pattern.*—Spreading and prolific, with 4 to 5 laterals after pinch.

B. Foliage:

*Color (upper surface).*—147A.

*Color (under surface).*—147B.

Shape.—See photograph.

CHART A

COMPARISON OF JASPER AND LUCIDO

| CULTIVAR | JASPER | LUCIDO |
|---|---|---|
| Ray floret color | Red | Red |
| Capitulum form and type | Flat anemone | Flat daisy |
| Diameter across face of capitulum | 64 to 70 mm | 70 to 83 mm |
| Flowering response | 53 to 60 days | 56 to 60 days |
| Plant height with 14 to 17 long days | 23 to 33 cm | 23 to 30 cm |
| Branching pattern | 4 to 5 laterals | 5 laterals |
| Recommended use | Spray pot mum | Spray pot mum |

COMPARISONS MADE OF PLANTS GROWN AS PINCHED SPRAY POT MUMS IN SALINAS, CALIFORNIA

I claim:

1. A new and distinct Chrysanthemum plant named Jasper, as described and illustrated.

* * * * *

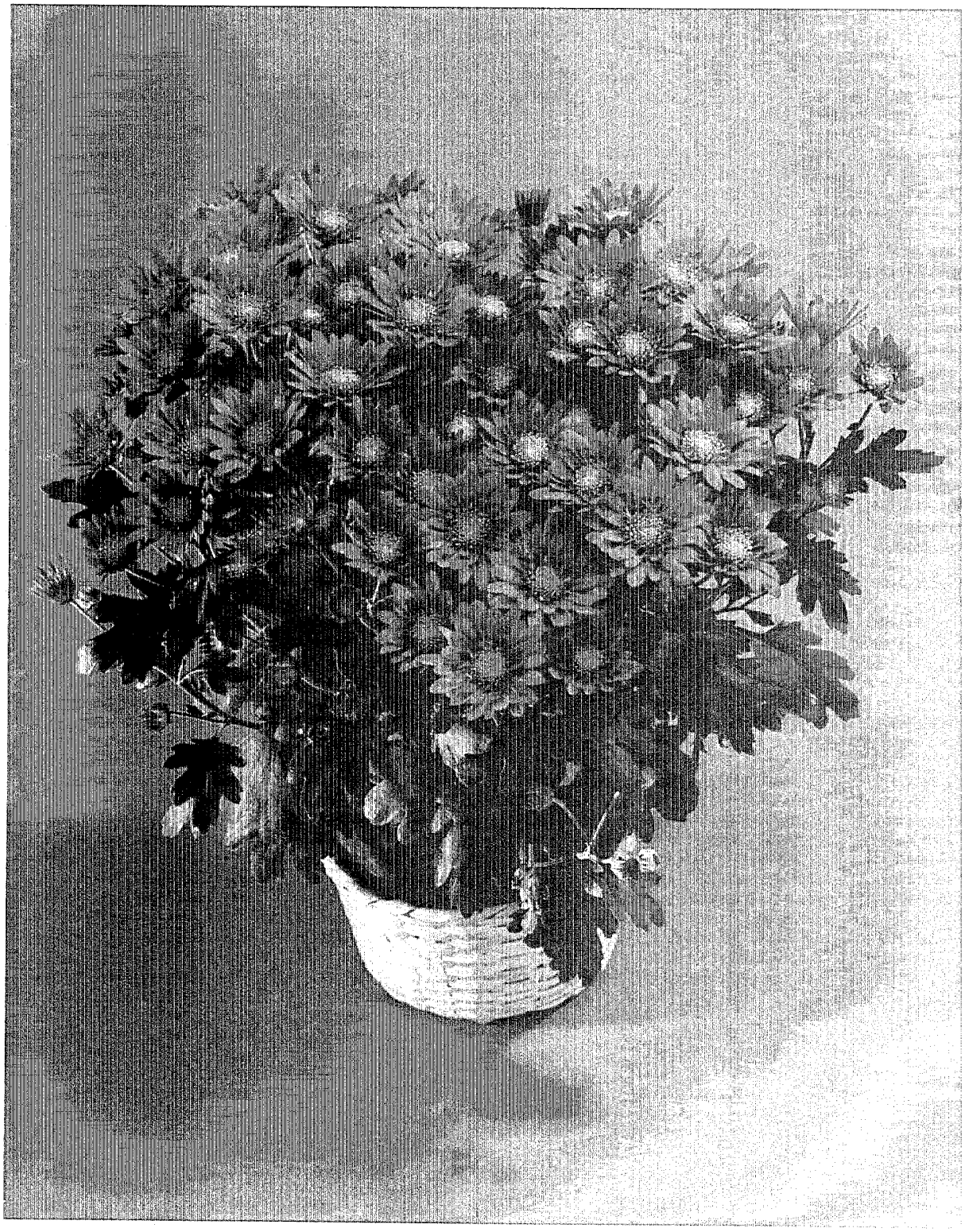

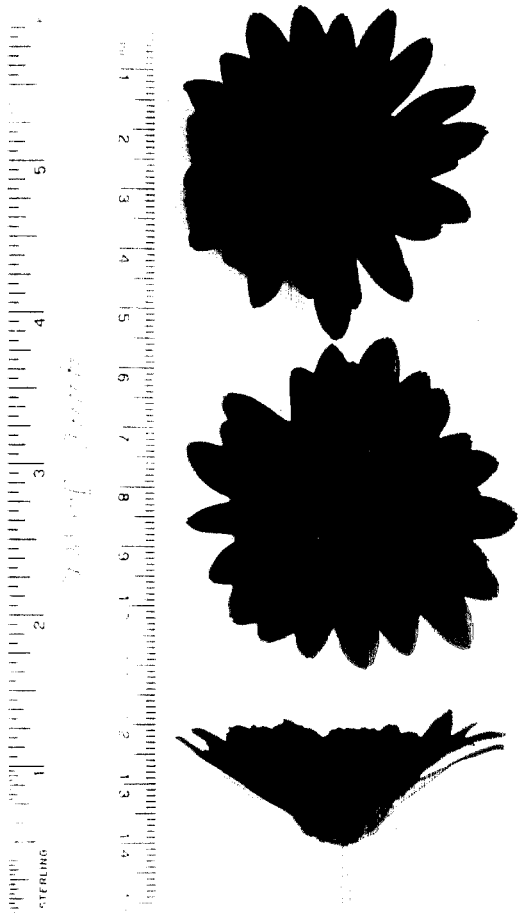
STERLING

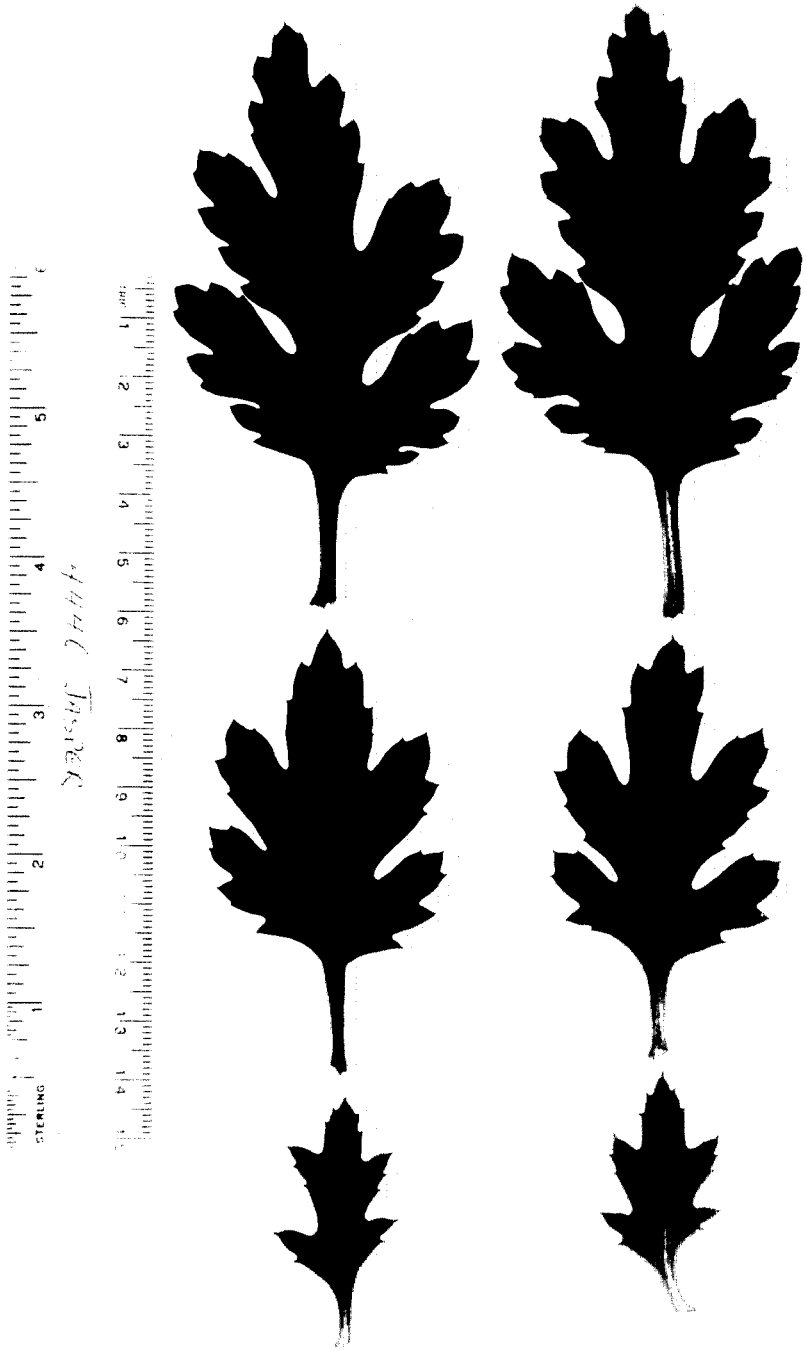
STERLING